United States Patent
Ray et al.

(10) Patent No.: US 9,041,926 B2
(45) Date of Patent: May 26, 2015

(54) APPARATUS AND METHOD FOR IN-FLIGHT DETECTION OF AIRBORNE VOLCANIC ASH

(71) Applicant: Rosemount Aerospace Inc., Burnsville, MN (US)

(72) Inventors: Mark D. Ray, Burnsville, MN (US); Kaare J. Anderson, Farmington, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 0 days.

(21) Appl. No.: 14/178,580

(22) Filed: Feb. 12, 2014

(65) Prior Publication Data

US 2015/0070700 A1 Mar. 12, 2015

Related U.S. Application Data

(60) Provisional application No. 61/874,438, filed on Sep. 6, 2013.

(51) Int. Cl.
| | |
|---|---|
| *G01N 21/00* | (2006.01) |
| *G01N 21/53* | (2006.01) |
| *B64D 47/00* | (2006.01) |

(52) U.S. Cl.
CPC ............... *G01N 21/53* (2013.01); *B64D 47/00* (2013.01)

(58) Field of Classification Search
CPC ............... G01N 21/53; G01N 21/538; G01N 2021/4709; G01N 15/0205; G01N 21/21
USPC .......................................... 356/342
See application file for complete search history.

(56) References Cited

U.S. PATENT DOCUMENTS

| | | | |
|---|---|---|---|
| 7,986,408 B2 | 7/2011 | Ray et al. | |
| 8,666,570 B1 * | 3/2014 | Tillotson | 701/14 |
| 2012/0182544 A1 | 7/2012 | Asahara et al. | |

* cited by examiner

*Primary Examiner* — Tarifur Chowdhury
*Assistant Examiner* — M D Rahman
(74) *Attorney, Agent, or Firm* — Locke Lord LLP; Scott D. Wofsy; Joshua L. Jones

(57) ABSTRACT

A method of optically determining the presence of volcanic ash within a cloud comprises emitting a circularly polarized illuminating beam within a cloud and analyzing backscatter light to identify the presence of volcanic ash within the cloud. The method further includes determining the degree to which the cloud has altered the polarization state of the emitted beam. The index of refraction of the backscatter light and the opacity of the backscatter light are also analyzed.

9 Claims, 1 Drawing Sheet

1

APPARATUS AND METHOD FOR IN-FLIGHT DETECTION OF AIRBORNE VOLCANIC ASH

CROSS-REFERENCE TO RELATED APPLICATIONS

This application claims the benefit of and priority to U.S. Provisional Patent Application No. 61/874,438 filed Sep. 6, 2013, which is incorporated by reference herein in its entirety.

BACKGROUND OF THE INVENTION

1. Field of the Invention

The present invention relates to sensors, e.g., in-flight sensors on board an aircraft, and more particularly to detecting the content of clouds.

2. Description of Related Art

Airborne volcanic ash is a serious threat to aircraft safety, as evidenced by the flame-out of all four engines of KLM Flight 867 in 1989, and a major disruption to air traffic, as was apparent during the eruption of the Iceland volcano Eyjafjallajokull in 2010. While satellites and meteorology stations report dangerous levels of ash to air traffic controllers, a sensor on board the aircraft to alert pilots of the presence of hazardous levels of ash is highly desirable. Satellite scans of a particular area are typically updated only twice per day, and meteorology stations sample the air over a limited angle above the station.

Several references describe various in-situ apparatuses and methods for determining the presence of large water droplets and icing conditions from an aircraft. However none of these references describe methods or devices for determining the presence of volcanic ash which is potentially as hazardous to an aircraft in-flight. The closest prior art is U.S. Pat. No. 7,986,408 owned by Rosemount Aerospace, Inc., hereby incorporated by reference in its entirety, which describes an airborne laser sensor for detecting and distinguishing liquid water droplets from ice crystals using circularly polarized light.

Such conventional methods and systems have generally been considered satisfactory for their intended purpose. However, there is still a need in the art for an in-flight detection systems and methods that allow for improved detection of cloud content, including volcanic ash. There also remains a need in the art for such a systems and methods that are easy to make and use. The present disclosure provides a solution for these problems.

SUMMARY OF THE INVENTION

A method of optically determining the presence of volcanic ash within a cloud includes emitting a circularly polarized illuminating beam within a cloud and analyzing backscatter light to identify the presence of volcanic ash within the cloud. The step of analyzing can further include determining the circular polarization of the backscatter light. The step of analyzing can further include determining the degree to which the cloud has altered the polarization state of the emitted beam to distinguish between liquid and solid.

In certain embodiments, the step of analyzing can further include measuring the index of refraction from the backscatter light to distinguish between ice and volcanic ash. For example, an index of refraction between 1.5 to 1.6, as determined from the backscatter light, can indicate the presence of volcanic ash. In certain embodiments, the step of analyzing includes measuring the opacity of the backscatter light to distinguish between ice and volcanic ash.

The step of emitting can include directing a circularly polarized laser light beam into a volume of space of the cloud. The step of analyzing can include analyzing the backscatter signal to identify the presence of volcanic ash within the cloud by determining the degree to which the cloud has altered the polarization state of the emitted beam.

An apparatus for in-flight detection of airborne volcanic ash includes an optical beam emitter configured to output a circularly polarized light beam into a cloud and an optical receiver configured to receive backscatter signal from the light beam. A processor is operatively connected to the optical receiver to analyze the backscatter light to identify the presence of volcanic ash within the cloud. The processor can be configured to determine the circular polarization of the backscatter light. The processor can be configured to determine the degree to which the cloud has altered the polarization state of the emitted beam. The processor can also be configured to measure the index of refraction and the opacity of the backscatter light.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
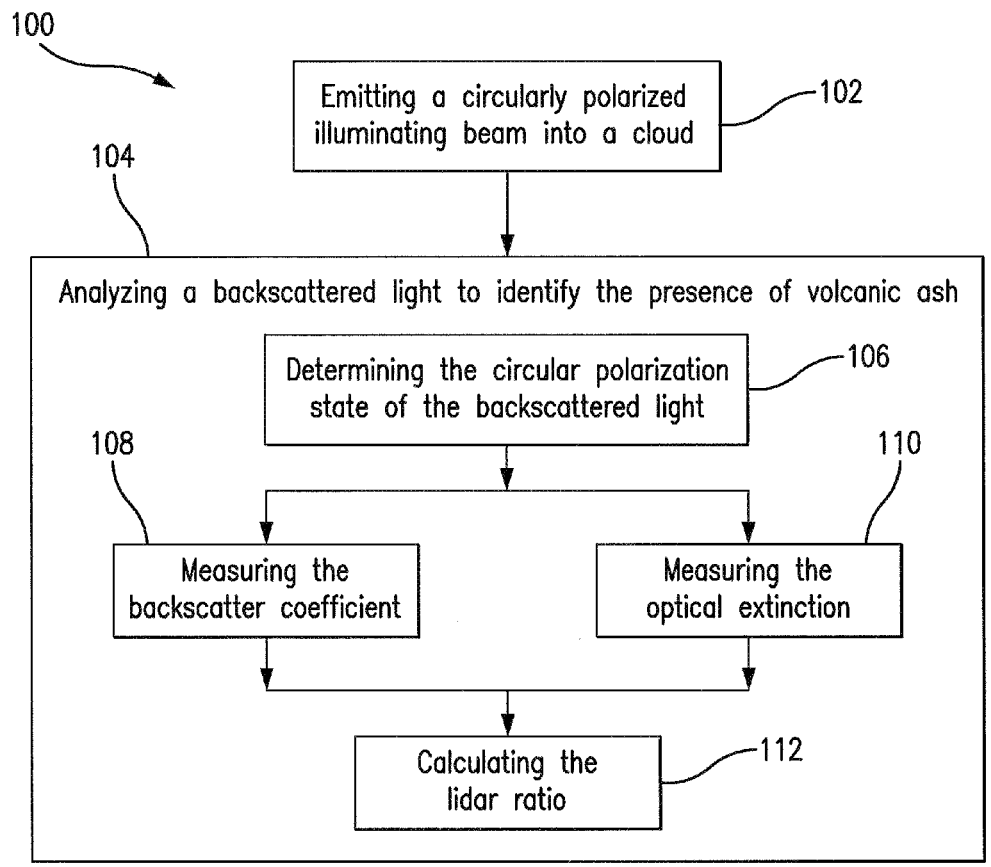
FIG. 1 is a flow chart illustrating an exemplary embodiment of a method in accordance with the present disclosure.

Reference will now be made to the drawings wherein like reference numerals identify similar structural features or aspects of the subject disclosure. For purposes of explanation and illustration, and not limitation, a partial view of an exemplary embodiment of an apparatus and method for in-flight detection of airborne volcanic ash in accordance with the disclosure is shown in FIG. 1 and is designated generally by reference character 100. Other embodiments of the system in accordance with the disclosure, or aspects thereof, are provided in FIG. 2, as will be described. The systems and methods described herein can be used determine the presence of volcanic ash within a cloud.

The following are hereby incorporated by reference in their entirety: U.S. Pat. Nos. 7,986,408, 8,144,325, 8,338,785, as well as U.S. Patent Applications 2013/0103317 and 2013/0103316.

A sensor that can look ahead of the aircraft far enough to give pilots sufficient reaction time to avoid an ash cloud is ideal, but a sensor that performs other safety functions, such as alerting the crew to the presence of supercooled large droplets or excessive quantities of ice crystals is still useful. All of these conditions can be hazardous to the aircraft.

In general, direct reflections of an illuminating light, such as laser light, from spherical water droplets are purely specular while those from ice crystals and volcanic ash are not.

Water droplets ideally act like perfect mirrors and scatter the reflected laser light back on itself without altering the polarization state. If the incident light is horizontally or vertically polarized, the reflected light is likewise horizontally or vertically polarized. Therefore, a backscatter polarization with a relatively low degree of depolarization is indicative of a liquid water cloud. In the case of circular polarization, the direction of the rotating electric field does not change upon reflection, but the change in Poynting vector of the incident wave changes the sense of circular polarization upon reflection. Hence, an incident beam which is right hand circularly polarized becomes left hand circularly polarized upon reflection, and vice versa.

Ice crystals, on the other hand, tend to alter the polarization state of reflected light, due in part to multiple internal reflections from their facets and in part to the birefringence of ice. Reflected light from airborne ice crystals becomes a mixture of two orthogonal polarization states when the incident light is a pure polarization state. By monitoring both orthogonal polarization states of the backscatter light, it is possible to distinguish water droplets from ice crystals.

Similar to ice crystals, volcanic ash particles are solid and depolarize light because of their irregular shape. Airborne ash particles are 10 to 30 μm diameter so the ratio of ash particle size to laser wavelength is roughly the same as for water droplets. Therefore, besides depolarization, the main difference between volcanic ash clouds and water clouds are the index of refraction and the opacity of the ash. The index of refraction for volcanic ash is n=1.5 to 1.6 versus n=1.35 for water and ice. Further, the opacity of ash is roughly 10,000 times greater than that of water and ice.

These differences are illustrated when analyzing circularly polarized light backscatter from a cloud. Circularly polarized light is advantageous because the fourth Stokes parameter (V), a measure of the degree of circular polarization, is more sensitive to changes in cloud phase (i.e. liquid or solid) than is linear depolarization. The intrinsic backscattering depolarization d of the cloud produces a measured linear depolarization LD such that LD=d/(2−d) while the corresponding Stokes parameter V for circular polarization is V=2d−1. The relationship between LD and V is not simple proportionality, but it is clear from the leading coefficient of d in both equations that V is more sensitive to depolarization than LD. Therefore, the use of circular polarization light and the measure of the degree of circular polarization (V) provides a better indication of the presence of volcanic ash versus linear polarization.

The method of optically determining the presence of volcanic ash within a cloud in accordance with an exemplary embodiment of the present disclosure is shown in FIG. 1. Flow chart 100 illustrates the steps to detect the presence of volcanic ash within a cloud. First, at step 102, a circularly polarized laser light illuminating beam is emitted within a cloud. Next, at step 104, the backscatter light received from the laser light beam is analyzed to identify the presence of volcanic ash.

The step of analyzing 104 includes step 106 which includes determining the degree to which the cloud has altered the polarization state of the emitted beam to distinguish between liquid and solid particles within the cloud. In the event step 106 results in a determination of the presence of solids, analyzing further includes step 108 for measuring the index of refraction from the backscatter light wherein the index of refraction for identifying volcanic ash is 1.5 to 1.6 to distinguish between ice and volcanic ash. Finally, analyzing the backscatter light may include step 110 of measuring the opacity of the backscatter light to distinguish between ice and volcanic ash. Step 110 can be used in addition or in lieu of step 108 and vice versa.

Figure 2:
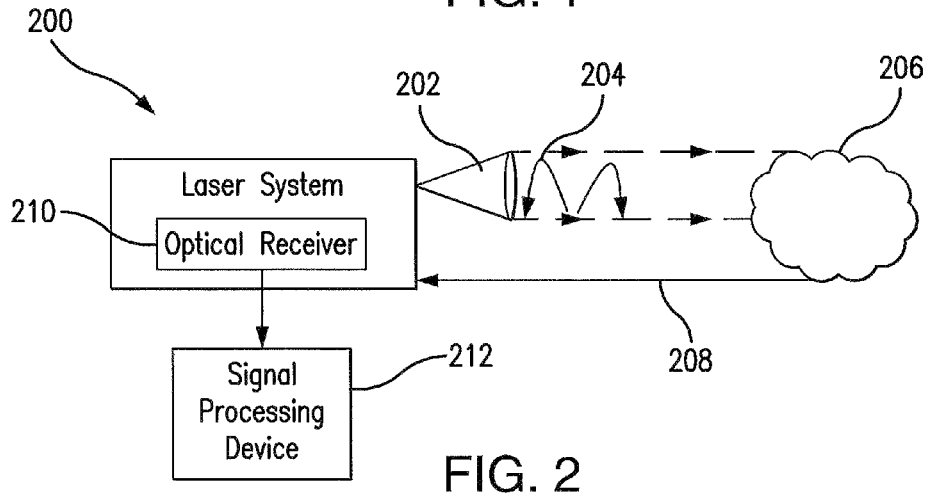
FIG. 2 is a schematic of an optical device for performing the method of FIG. 2 using circular polarization.

Referring now to FIG. 2, a schematic illustration of an apparatus 200 configured to perform the method according to the present invention. An optical beam emitter 202 directs circularly polarized light 204 into a cloud 206. A backscatter signal 208 is received with an optical receiver 210. A signal processing device 212 operatively connected to the optical receiver 210 analyzes the backscatter signal to determine the presence of volcanic ash within the cloud as described above.

The methods and systems of the present disclosure, as described above and shown in the drawings provide for in-flight detection of volcanic ash within a cloud. While the apparatus and methods of the subject disclosure have been shown and described with reference to preferred embodiments, those skilled in the art will readily appreciate that changes and/or modifications may be made thereto without departing from the spirit and scope of the subject disclosure.

What is claimed is:

1. A method of optically determining presence of volcanic ash within a cloud, comprising:
   emitting a circularly polarized illuminating beam within the cloud; and
   analyzing backscatter light to identify the presence of volcanic ash within the cloud,
   wherein the step of analyzing comprises determining a degree to which the cloud has altered a polarization state of the emitted beam to distinguish between liquid and solid and measuring an index of refraction from the backscatter light to distinguish between ice and volcanic ash.

2. The method as recited in claim 1, wherein the step of analyzing includes determining circular polarization of the backscatter light.

3. The method as recited in claim 1, wherein the index of refraction is 1.5 to 1.6.

4. The method as recited in claim 1, wherein the step of analyzing includes measuring opacity of the backscatter light to distinguish between ice and volcanic ash.

5. The method as recited in claim 1, wherein the step of emitting includes:
   directing a circularly polarized laser light beam into a volume of space of the cloud.

6. An apparatus for in-flight detection of airborne volcanic ash, comprising:
   an optical beam emitter configured to output a circularly polarized light beam into a cloud;
   an optical receiver configured to receive backscatter light from the emitted beam; and
   a processor operatively connected to the optical receiver to analyze the backscatter light to identify presence of volcanic ash within the cloud, wherein the processor is configured to determine a degree to which the cloud alters a polarization state of the emitted beam and measure an index of refraction from the backscatter light to distinguish between ice and volcanic ash.

7. The apparatus as recited in claim 6, wherein the processor is configured to determine circular polarization of the backscatter light.

8. The apparatus as recited in claim 6, wherein the processor is configured to detect volcanic ash with a measured index of refraction between 1.5 to 1.6.

9. The apparatus as recited in claim 6, wherein the processor is configured to measure opacity of the backscatter light.

* * * * *